US00PP27187P3

(12) United States Plant Patent
Francis

(10) Patent No.: US PP27,187 P3
(45) Date of Patent: Sep. 27, 2016

(54) APPLE TREE NAMED 'PINK CHIEF'

(50) Latin Name: ***Malus domestica* Borkh.**
Varietal Denomination: Pink Chief

(71) Applicant: Fruit Varieties International Pty Ltd, Grove, Tasmania (AU)

(72) Inventor: Brendon Francis, Grove (AU)

(73) Assignee: FRUIT VARIETIES INTERNATIONAL PTY LTD, Dover, Tasmania (AU)

( * ) Notice: Subject to any disclaimer, the term of this patent is extended or adjusted under 35 U.S.C. 154(b) by 143 days.

(21) Appl. No.: 14/120,696

(22) Filed: Jun. 16, 2014

(65) Prior Publication Data

US 2015/0082499 P1 Mar. 19, 2015

Related U.S. Application Data

(60) Provisional application No. 61/960,435, filed on Sep. 17, 2013.

(51) Int. Cl.
*A01H 5/08* (2006.01)

(52) U.S. Cl.
USPC ..... Plt./161
CPC ..... *A01H 5/0875* (2013.01)

(58) Field of Classification Search
USPC ..... Plt./161
See application file for complete search history.

*Primary Examiner* — Keith Robinson
(74) *Attorney, Agent, or Firm* — Phase M, LLP

(57) ABSTRACT

A new and distinct apple tree (*Malus domestica* Borkh) named 'Pink Chief'. The new variety is a spontaneous limb mutation of 'Cripps Pink' and is distinguished by its highly colored pink-red fruit, weaker vigor and columnar bearing.

6 Drawing Sheets

Latin name: *Malus domestica* Borkh.

Variety denomination: 'Pink Chief'.

BACKGROUND OF THE VARIETY

'Pink Chief' is a new and distinct cultivar of apple tree *Malus domestica* Borkh. This new variety is a spontaneous limb mutation of 'Cripps Pink' (U.S. Plant Pat. No. 7,880). 'Pink Chief' was first observed in a 'Cripps Pink' orchard in Dover, Tasmania, Australia in 2007, where it was distinguished by its highly colored fruit. Asexual reproduction of the new variety was carried out by bud grafting in 2009 and trees of the new variety were planted for additional observation at Lucaston, Tasmania, Australia. It was found that the new variety is also distinguished from its parent by its weaker vigor and columnar bearing. 'Pink Chief' has since been fruited through successive asexually propagated generations at Lucaston and has been observed to remain true to type.

BRIEF DESCRIPTION OF THE VARIETY

The new variety claimed herein is primarily distinguished by its intense pink-red fruit color and columnar bearing. These and other distinguishing characteristics are set forth in the tables below.

'Pink Chief' is distinguishable from its parent 'Cripps Pink' as described in Table 1 below:

TABLE 1

Comparison of 'Pink Chief' to 'Cripps Pink'

| Characteristic | 'Cripps Pink' (U.S. Plant Pat. No. 7,880) | 'Pink Chief' |
|---|---|---|
| Tree vigor | Medium to strong | Very weak to weak |
| Tree type/bearing | Ramified/spurs & long shoots | Columnar/spurs only |
| 1 year old shoot: Internode length | Medium | Short |
| Fruit-area of overcolor | Small | Large |
| Fruit-intensity of overcolor | Light | Medium |
| Fruit-stalk length | Long | Short to medium |
| Fruit-stalk thickness | Thin | Thick |

A comparison of 'Pink Chief' to 'PLFOG99' (syn. 'Pink Belle', U.S. Plant Pat. No. 21,555), the most similar variety of common knowledge, is set forth in Table 2 below:

TABLE 2

Comparison of 'Pink Chief' to 'PLFOG99'

| Characteristic | 'PLFOG99' (syn. 'Pink Belle' U.S. Plant Pat. No. 21,555) | 'Pink Chief' |
|---|---|---|
| Fruit-area of overcolor | Small | Large |
| Fruit-intensity of overcolor | Light | Medium |
| Fruit stalk length | Long | Short to medium |
| Fruit stalk thickness | Thin | Thick |
| Depth of stalk cavity | Medium to deep | Shallow to medium |
| Eye basin depth | Shallow to medium | Medium to deep |
| Eye basin width | Narrow to medium | Medium to broad |
| Tree vigor | Weak to medium | Very weak to weak |

BRIEF DESCRIPTION OF THE PHOTOGRAPHS

DETAILED BOTANICAL DESCRIPTION OF THE VARIETY

Figure 1:
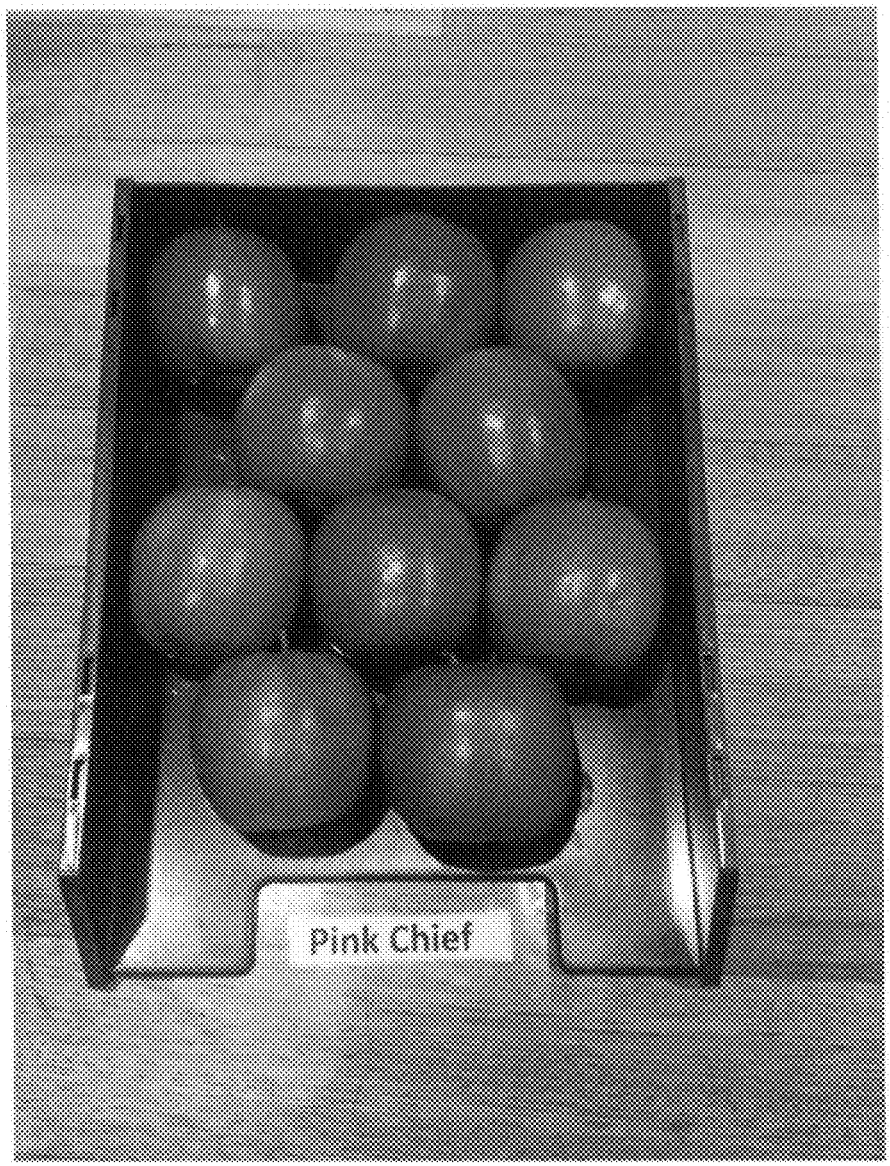
FIG. 1 shows current season's fresh fruit of 'Pink Chief' harvested at maturity.
Figure 2:
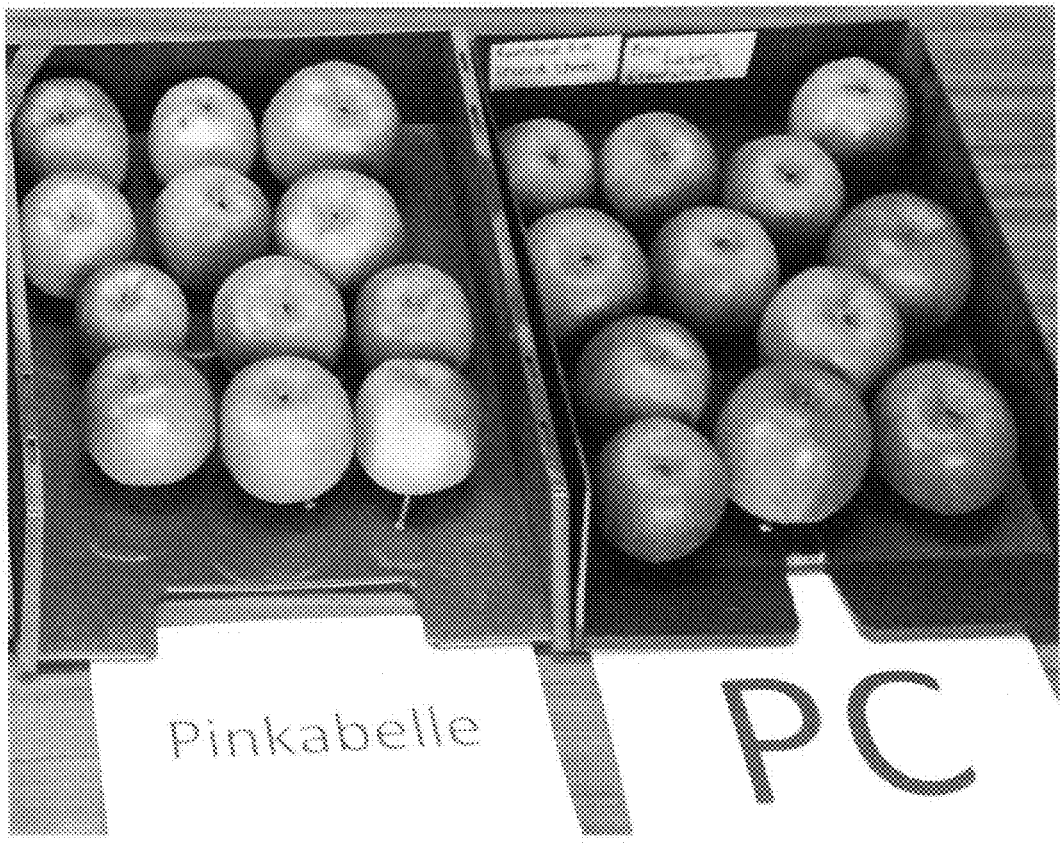
FIG. 2 shows current season's fresh fruit of 'Pink Chief' ("PC" on the right) compared to fruit of 'PLFOG99' ("Pinkabelle" on the left), both harvested at maturity.
Figure 3:
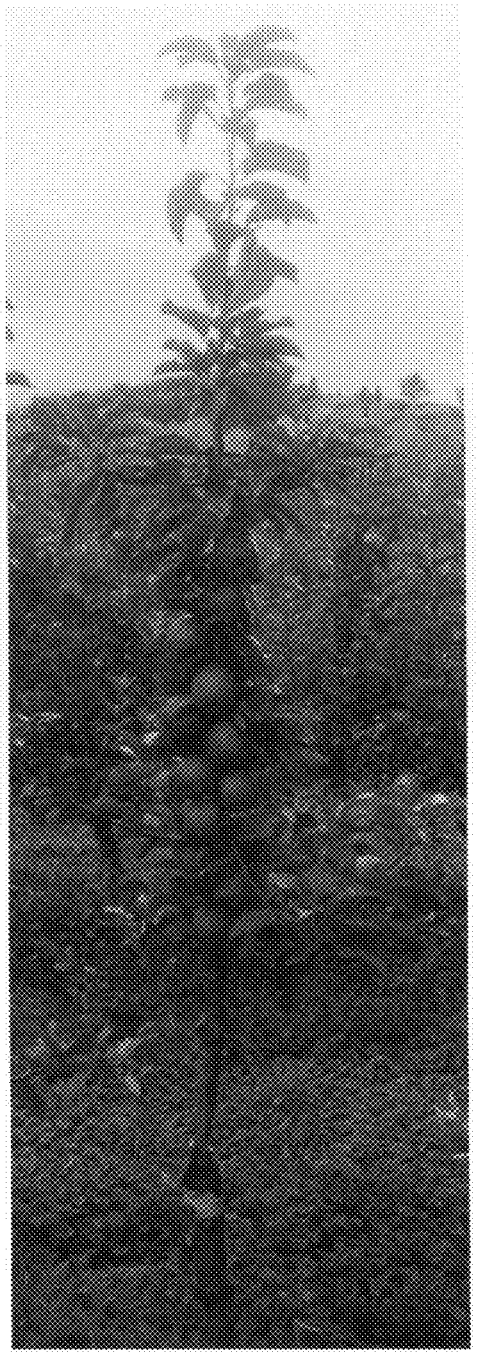
FIG. 3 shows a tree of 'Pink Chief' in its third growing season on MM106 rootstock.
Figure 4:
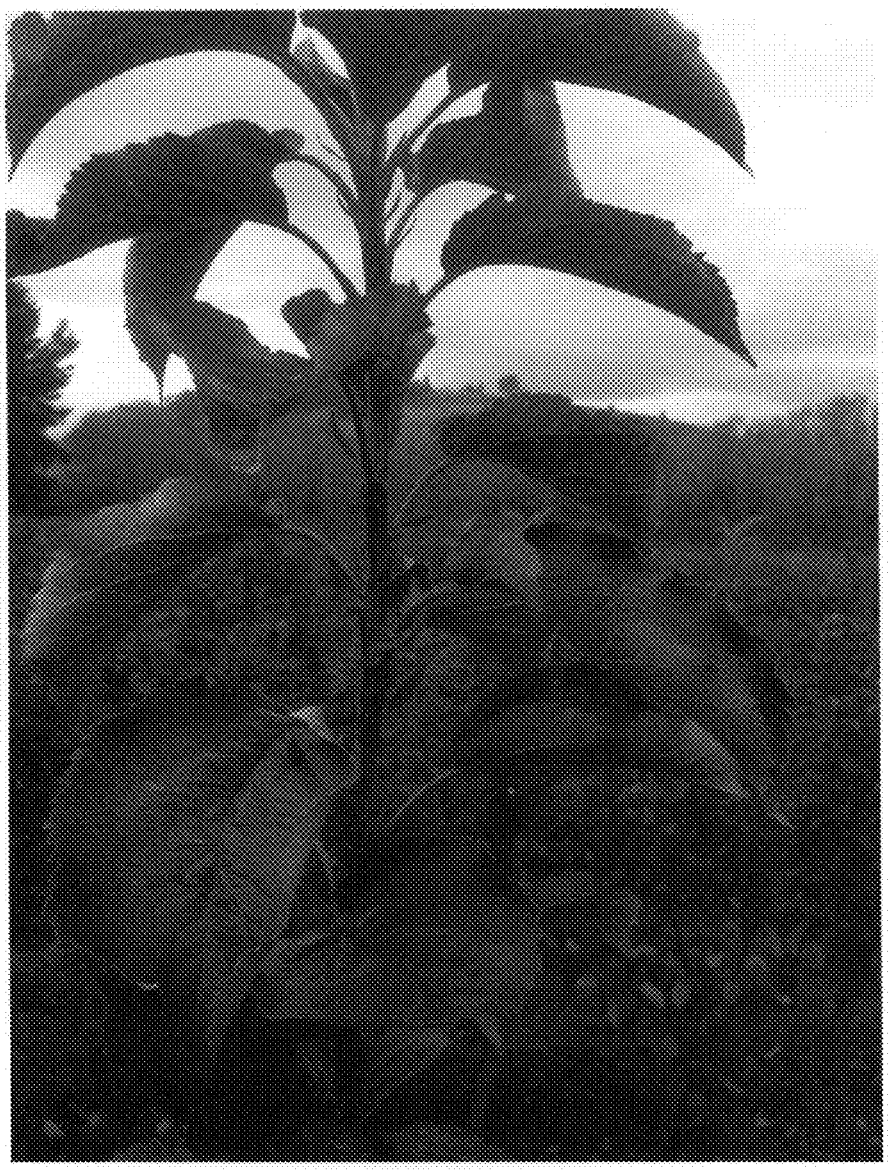
FIG. 4 shows leaves of a one year old current season's shoot of 'Pink Chief' in its third growing season on MM106 rootstock.
Figure 5:
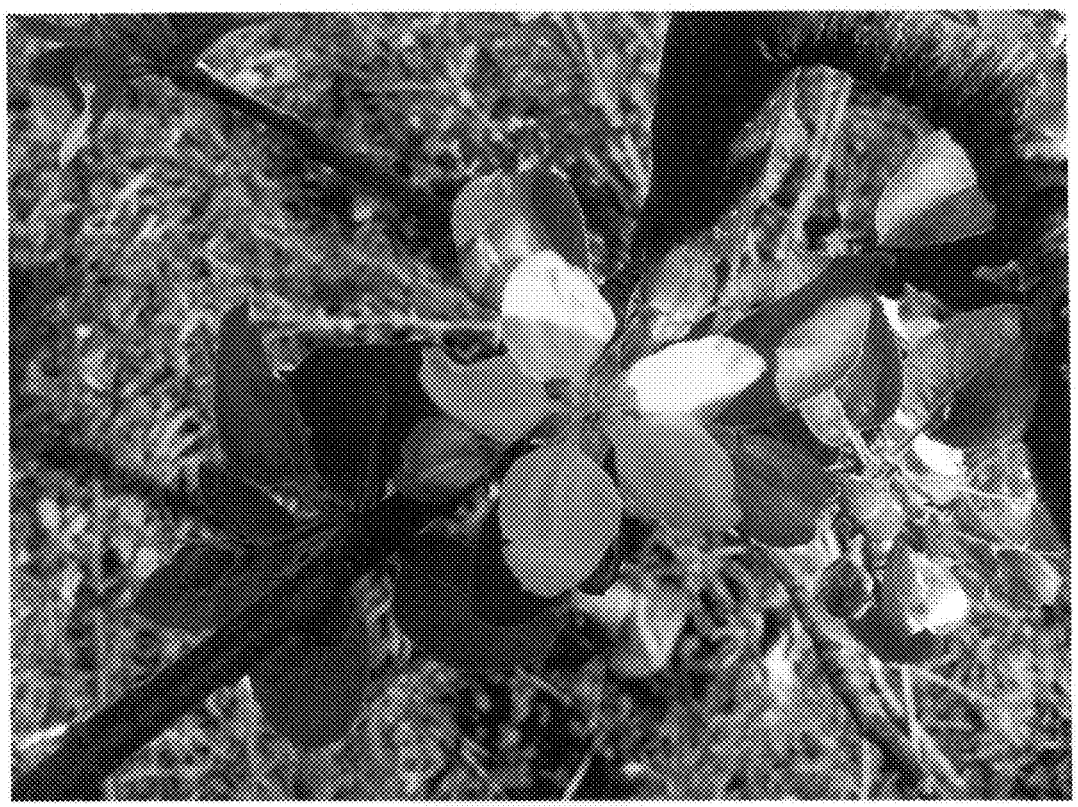
FIG. 5 shows a blossom of 'Pink Chief' on a 'Pink Chief' tree in its third growing season on MM106 rootstock; and, FIG. 6 shows fruit of 'Pink Chief' on a 'Pink Chief' tree in its third growing season on MM106 rootstock.
Figure 6:
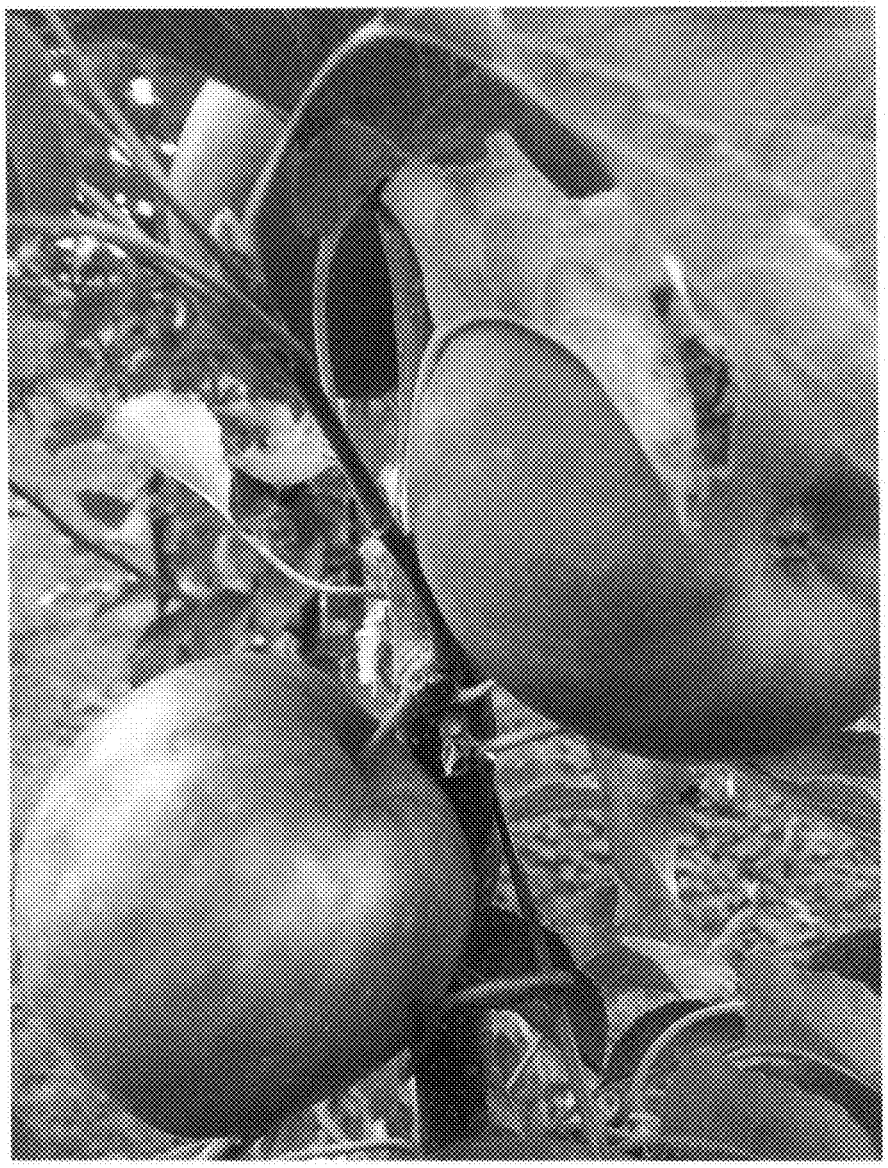

The following-detailed botanical description is based on observations made during the 2013 and 2014 growing seasons at Lucaston, Tasmania, Australia of three-year-old trees planted on 'MM106' rootstock (not patented). All colors are described according to The Royal Horticultural Society Colour Chart ($5^{TH}$ edition 2007). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor*.—Very weak to weak.
*Type*.—Columnar, bearing on spurs only.
*Habit*.—Very upright.
*Height*.—2.5 m.
*Trunk diameter*.—2.35 cm.
*Bark texture*.—Smooth with some ridging.
*Bark color*.—Greyed-orange 166A on sun exposed side and Greyed-brown 199A on shaded side.

Branch (fruiting branches located at around 1 m above the graft union):

*Length*.—10 to 37 cm.
*Diameter*.—6 mm at base.
*Crotch angle*.—Very upright branches on pruned tree; Branches on unpruned tree are horizontal to 10 degrees.
*Bark color*.—Greyed-orange 166A on sun exposed side and Greyed-brown 199A on shaded side.
*Lenticel length*.—1 mm.
*Lenticel color*.—Greyed-orange 174C.
*Quantity of lenticels per cm*$^2$.—8 to 12.

One year old shoot:

*Length*.—10 to 37 cm.
*Color*.—Greyed-orange 166A on sun exposed side and Greyed-brown 199A on shaded side.
*Pubescence*.—Weak to medium.
*Thickness*.—8 mm.
*Internode length*.—Very short; 1.8 to 2.1 cm.
*Number of lenticels per cm*$^2$.—8 to 12.

Flowers:

*Diameter of fully open flower*.—47 mm.
*Relative position of petal margin*.—Free to touching.
*Quantity of flowers per cluster*.—5 to 7.
*Date of beginning of flowering*.—Oct. 10, 2013 in Tasmania.
*Date of full bloom*.—Oct. 18, 2013 is Tasmania.
*Pollination requirement*.—Pollination required by another diploid variety flowering at similar time.

Petals:

*Quantity per flower*.—5.
*Shape*.—Ovate to ellipsoid.
*Length*.—24 mm.
*Width*.—14 mm.
*Apex*.—Ovoid
*Base*.—Cuneate to obovate at base.
*Margin*.—Smooth.
*Color*.—Upper surface — Red-purple 65D.
*Color*.—Lower surface — Red-purple 65B.
*Pistils*.—10 mm long; Yellow-green 149B.
*Stigma*.—0.8 mm diameter; Yellow-green N144A.
*Position of stigma relative to anther*.—Same level.
*Style*.—5 fused at base; Pubescent at base; length 8 mm; Yellow-green 149B.
*Ovary*.—Pubescent; 1.7 mm diameter; Yellow-green 149B.
*Anthers*.—14 to 21 per flower; Width 1.2 mm; Length 2.0 mm; Abundant pollen present, Yellow 13B.
*Pedicel*.—Length 22 mm; Diameter 3 mm; Grey-red 180A on sun exposed side; Yellow-green 153A on shaded side.
*Sepals*.—Quantity 5; Length 5.5 mm; Yellow-green 144C with Red-purple 59C on tip; Recurved with smooth straight margin; Pubescent.

Leaves:

*Length*.—12 cm.
*Width*.—8 cm.
*Length/width ratio*.—3:2.
*Blade margin*.—Biserrate.
*Shape*.—Oval to obtuse.
*Apex*.—Acute in shape.
*Base*.—Obtuse in shape.
*Pubescence*.—Lightly pubescent on underside.
*Color*.—Upper surface — Yellow-green 147B.
*Color*.—Lower surface — Yellow-green 146C.
*Attitude in relation to shoot*.—Outward.
*Petiole*.—Length 36 mm; Diameter 1.7 mm; Greyed-purple 184B.

Fruit:

*Quantity per cluster*.—5 to 7 per cluster if no thinning occurs.
*Diameter*.—79 mm.
*Height*.—86 mm.
*Ratio of height to width*.—About 1:1.
*General shape in profile*.—Cylindrical.
*Position of maximum diameter*.—Near center.
*Ribbing*.—Moderate.
*Crowning at calyx end*.—Moderate.
*Size of eye*.—Medium to large, 10.6 mm.
*Aperture of eye*.—Mostly closed, occasionally open.
*Length of sepal*.—Medium, 5.5 mm average length.
*Bloom of skin*.—Absent or weak.
*Greasiness of skin*.—Absent or weak.
*Background color of skin*.—Yellow-green 150C.
*Amount of over color*.—Medium to high, about 85%.
*Over color of skin*.—Red 46A.
*Intensity of over color*.—Medium to dark.
*Pattern of over color*.—Solid flush.

*Amount of russet around stalk cavity*.—Low to medium.
*Amount of russet on cheeks*.—Absent or small.
*Area of russet around eye basin*.—Absent or small.
*Length of stalk*.—Short to medium, 22 mm.
*Thickness of stalk*.—Thick, 3 mm.
*Stalk color*.—Greyed-orange 165A.
*Depth of stalk cavity*.—9 mm.
*Width of stalk cavity*.—Narrow to medium, 35 mm.
*Depth of eye basin*.—Medium to deep, 7.4 mm.
*Width of eye basin*.—Medium to broad, 33 mm.
*Flesh color*.—Yellow 11D.
*Firmness of flesh*.—9.5 kg, Firm.
*Flesh texture*.—Firm and crisp.
*Aroma*.—Fresh.
*Juiciness*.—Ample.
*Total soluble solids*.—15° Brix.
*Seeds*.—Minimum of 1, mostly 2 per cell; 9 per fruit; Acute; Greyed-orange 167B; Aperture of locules closed or slightly open.

Harvest:
*Harvest date*.—Time of Eating Maturity — Late season (Apr. 24, 2014 in Tasmania, Australia).
*Number of picks*.—One.
*Yield*.—18.5 kg from a typical three-year-old tree.
*Disease/insect resistance/susceptibility*.—No resistance/susceptibility noted.
*Market use*.—Fresh.

I claim:

1. A new and distinct apple tree substantially as described and illustrated herein.

* * * * *